United States Patent [19]
McConn-Stern et al.

[11] Patent Number: 5,879,717
[45] Date of Patent: Mar. 9, 1999

[54] WOUND HEALING COMPOSITIONS CONTAINING IODINE AND SUCROSE

[75] Inventors: Rita McConn-Stern, Greenlane, Kinara, Co. Galway, Ireland; Thomas C. Walsh, Salalah, Oman

[73] Assignee: Rita McConn-Stern, Galway, Ireland

[21] Appl. No.: 864,352

[22] Filed: May 28, 1997

Related U.S. Application Data

[63] Continuation of Ser. No. 495,682, filed as PCT/GB94/00261 Feb. 10, 1994 published as WO94/7811 Aug. 18, 1994, abandoned.

[30] Foreign Application Priority Data

Feb. 10, 1993 [GB] United Kingdom .................. 9302620

[51] Int. Cl.⁶ ......................... A61K 33/36; A61K 31/715
[52] U.S. Cl. ..................... 424/667; 424/668; 424/669; 424/670; 424/671; 424/672; 514/53; 514/738; 514/772
[58] Field of Search .............................. 514/53, 772, 738; 424/667, 670, 671, 668, 669, 672

[56] References Cited

U.S. PATENT DOCUMENTS 4,401,651  8/1983  Kuntson .

FOREIGN PATENT DOCUMENTS 0 258 761  3/1988  European Pat. Off. .
WO 88/04168  6/1988  WIPO .

OTHER PUBLICATIONS

Budavari et al. "The Merck Index" (11th Ed.) Merck & Co., Inc., Rahway, NJ (1989), pp. 705 and 1247.
Olin et al. "Facts and Comparisons," loose leaf drug information service, J.B. Lippincott Co., St. Louis, Mo. (1989) p. 49e.
Database WPI, Week 8315, Derwent Publications, Ltd., London, GB, AN83–36024K (15), Abstract, JP,A,58 039 620 (Matsui T.) Mar. 8, 1993.

*Primary Examiner*—Raymond J. Henley, III
*Assistant Examiner*—M. Moezie

[57] ABSTRACT

A wound-healing preparation comprises a solution or paste of a non-reducing sugar and iodine in a vehicle consisting essentially of a pharamcologically acceptable glycol, especially glycerol, and, optionally, water. Preferably, the sugar is sucrose, especially that obtained from sugar beet, and the vehicle is substantially anhydrous glycerol. In one preferred embodiment, the preparation is in the form of a veterinary infusible solution and is particularly useful in the treatment of mastitis. In another embodiment, surgical sutures are treated by coating with the preparation to prevent the presence or abscesses around surgical suture lines.

14 Claims, No Drawings

WOUND HEALING COMPOSITIONS CONTAINING IODINE AND SUCROSE

This application is a continuation of application Ser. No.08/495,682, filed Aug. 3, 1995, now abandoned, which is a 371 of PCT/GB94/00261 filed Feb. 10, 1994 published as WO94/7811 Aug. 18, 1994.

The present invention relates to sugar-containing liquid or paste preparations for the treatment of wounds and related conditions. It has particular, but not exclusive, application to veterinary medicine.

The use of various forms of sugar to treat wounds has been known since ancient times. The knowledge of such use appears to have been widespread because there are reports of honey or cane sugar being used in wound treatment by native American Indians, ancient Egyptians and Incas. However, it appears that, until fairly recently, the wound-healing properties of sugar have not been exploited in modern times.

GB-A-2048070 (corresponding to U.S. Pat. No. 4,401,651) discloses a wound-healing preparation comprising (a) 10 to 80 parts by weight of a saccharide antibacterial tissue nourisher with (b) 1 part by weight of an antifungal/antibacterial agent and (c) a sufficient amount of a carrier to impart a consistency which readily permits the preparation to be spread on and adhere to a sponge or gauze dressing and to remain in place when applied directly to tissue of an open wound or of a burn, the carrier comprising at most ⅓ of the weight of the preparation. The preferred saccharide is an ordinary granulated sugar, the preferred antifungal/antibacterial agent is povidone-iodine and the preferred carrier is water or an ointment base. The exemplified formulation comprises 20 parts by weight granulated sugar, 5 parts by weight Betadine® ointment and 2 parts by weight Betadine® solution. Both Betadine® ointment and Betadine® solution contain 10 wt % povidone-iodine. A development of this product is available from Sugardyne Pharmaceuticals Inc. (Greenville, Miss. 38701, USA) as SUGARDYNE® and is believed to be substantially identical with said exemplified formulation.

Glycerol and propylene glycol are included amongst a list of about 30 components from which the carrier may be formulated. U.S. Pat. No. 4,401,651, but not GB-A-2048070, includes iodine tincture amongst antifungal/antibacterial agents suitable for wholly or partially replacing povidone-iodine.

EP-A-258761 (corresponding to U.S. Pat. No. 4,844,898) discloses an improved wound-healing preparation based on that of GB-A-2048070/ U.S. Pat. No. 4,401,651). It contains 50 to 90 wt % of a sugar, 0.5 to 10 wt % povidone-iodine, 1 to 20 wt % water and a buffer to pH 3.5–6. The composition can comprise, inter alia, conventional excipients and the specified excipients include macrogols and glycerin. All four exemplified formulations include glycerol in an amount of 0.6 wt % or 1 wt % and polyethylene glycol and polyoxyethylene polyoxypropylene glycol in a combined amount of between 12 and 18 wt %.

K. R. Middleton and D. Seal (Pharm. J. 235 (1985) 757–758) report the use by Northwick Park Hospital (Harrow, UK) of thin and thick sugar pastes for wound-healing. The compositions of these pastes are as follows:

|  | thin paste | thick paste |
| --- | --- | --- |
| caster sugar | 1200 g | 1200 g |
| icing sugar | 1800 g | 1800 g |
| PEG 400 | 1416 ml | 686 ml |
| hydrogen peroxide (30%) | 23.1 ml | 19 ml. |

SUGARDYNE® is effective in both medical and veterinary use. However, the granular texture of the product is unattractive and makes it difficult to apply. More importantly, povidone-iodine makes the product too expensive for third world and veterinary use. We have found that a smoother product could readily be obtained by use of more finely ground sugar, such as caster or icing sugar. However, problems were encountered in seeking a cheaper alternative antifungal/antibacterial agent to povidone-iodine. Iodine tincture is a relatively cheap and inexpensive alternative. However, it imparts a dark purple-black colour to aqueous sugar paste and, on standing, develops a spongy surface layer and bubbles within the body of the paste. Surprisingly, it was found that this problem could be overcome by replacing part or all of the water content with a glycol such as glycerol or propylene glycol.

According to the present invention, there is provided a wound-healing preparation comprising a solution or paste of a reducing or non-reducing sugar and iodine in a vehicle consisting essentially of a pharmacologically acceptable glycol, especially glycerol or propylene glycol, and, optionally, water.

The sugar can be any of the reducing or non-reducing sugars used for wound-healing, for example dextrose, glucose, honey, molasses or sucrose, but usually will be sucrose. Although the sucrose can be cane sugar (ie. obtained from sugar cane), it is preferred to use beet sugar (ie. obtained from sugar beet). Further, although granulated sugar can be used, it is much preferred to use more finely ground sugar, such as caster or, especially, icing sugar.

The sugar content of the preparation will determine the rheological properties of the preparation. Thus, where a thick paste is required to cover a wound, the sugar content will be high but where an infusible solution is required for, for example, treatment of bovine mastitis, lower sugar concentrations will be used. Usually, the sugar concentration will range from 50 to 90% w/v with, for most applications, 60 to 85% w/v being preferred.

In non-aqueous preparations of the invention using glycerol as the vehicle, it has been found that the use of 100 ml to 600 ml glycerol to 500 g sugar is particularly preferred. At 100 to 150 ml glycerol per 500 g sugar, the preparation is particularly suitable for the formation of a bolus for filling dead space, especially for intrauterine use. At 200 to 350 ml glycerol per 500 g sugar, the preparation is particularly suitable for topical use, especially where there is extensive necrosis with either desiccation or major sepsis. At 350 to 600 ml glycerol per 500 g sugar, the preparation is an infusible solution, especially suitable for intramammary or body cavity infusion or injection. Other pharmacologically acceptable glycol will be used in respective amounts to provide equivalent rheological properties.

The rheological properties of the preparation also can be varied by the inclusion of water in the vehicle. Generally, the higher the water content, the more fluid the preparation for any given sugar content. However, at higher water contents, the preparations have an increasing tendency to separate. Usually, the water content will not exceed 50% of the vehicle and, for most purposes, it is preferred that the vehicle is substantially anhydrous or contains less than 30% water. The preferred vehicle is glycerol/water or, especially, glycerol.

Iodine is present in an antimicrobial concentration. Usually, the concentration will be 0.005 to 10 wt %, especially 0.01 to 5 wt %. For example, it can be added as Iodine Tincture U.S.P. (iodine 2 g, sodium iodide 2.4 g, ethanol 50 ml, water to 100 ml); Strong Iodine Tincture U.S.P. (iodine 7 g, potassium iodide 5 g, water 5 ml, ethanol to 100 ml); Iodine Topical Solution U.S.P. (iodine 2 g, sodium iodide 2.4 g, water to 100 ml); or Weak Iodine Solution B.P. (iodine 2.5 g, potassium iodide 2.5 g, water 2.5 ml, ethanol (90%) to 100 ml).

The preparation of the invention can readily be prepared by mixing the components together. Usually, the glycol is added to the sugar and the mixture stirred to form a paste or solution to which the iodine is subsequently added. Any water content of the vehicle can be added after or, preferably, before addition to the sugar. Although the formation of the sugar paste or solution can be carried out at elevated temperature, heating is usually not required. However, it is preferred to heat the glycol to, for example, 180° C. prior to addition of the iodine.

Usually, the preparations of the invention will consist essentially of the sugar, iodine and aforementioned vehicle components. However, other components can be present to improve, for example, stability, colour or appearance and to modify the Theological properties as required. In particular, the presence of a buffer, for example 0.1M disodium phosphate citrate, to pH 3.5 to 6 may be desired to prevent phase separation of the preparation on storage. Further, if required other actives, for example one or more analgesic, antibiotic, anti-inflammatory agent, astringent and corticosteroid, can be present. For some applications, it is preferred that the composition comprises one or more of copper sulphate, suitably in an amount of about 1 wt %; dexamethasone, suitably in an amount of about 0.1 wt %; and sodium salicylate, suitable in an amount of about 1 wt %.

Although the preparation of the present invention can be used for the medical uses specified in GB-A-2048070/U.S. Pat. No. 4,401,651 and EP-A-258761/U.S. Pat. No. 4,844,898, it is particularly useful for veterinary use. Examples of such use are provided in the Examples hereinafter.

It has also been found that the preparation is useful to coat surgical sutures prior to use in wound or other closures. The coating can be accomplished by simply drawing the surgical suture through the preparation immediately prior to use. Whereas the presence of abscesses around surgical suture lines are not uncommon in veterinary practice, there is a marked absence of such abscesses when the suture has been coated with a preparation of the invention.

It has also surprisingly been found that mastitis, especially bovine summer mastitis, and other mammary infections can be effectively treated by intra-mammary infusion of a preparation of the invention. Bovine summer mastitis is a fly-borne disease arising from a gram-positive infection in the breast tissue of non-lactating cows. It often leads to oedema, teat inflammation and large abscess formation. Standard treatment includes drainage, parenteral administration of antibiotics and, sometimes, amputation of the nipple. Often, prolonged drainage of antibiotic-resistant puss is required. However, simply retrograde infusion of, for example, 10 to 50 ml of a solution of the invention through the nipple usually results in cessation of puss production within a few days and replacement by a serous-sanguineous fluid. Further, relatively rapid reduction in breast size and fibrosis of the tissue is observed.

The following are non-limiting examples of the preparation and use of preparations of the invention.

EXAMPLE 1

| | |
|---|---|
| Icing sugar (beet) | 500 g |
| Water | 30 ml |
| Glycerol | 30 ml |
| Weak Iodine Solution BP | 10–15 ml |

The glycerol and water were mixed together and the mixture added to the sugar with stirring to form a thin paste into which the tincture of iodine was mixed. The process was conducted at room temperature.

The preparation is a slightly-thickened, free-flowing, mustard-yellow smooth liquid with a good shelf life and is suitable for a wide range of wound-healing uses.

In each of the following Examples 2 to 11, the glycerol was added to the sugar with stirring to form a solution to which the iodine solution was added. In Examples 3 to 8, the "iodine solution" contained 68 mg iodine, 68 mg potassium iodide, 6.8 ml water in ethanol to 100 ml.

EXAMPLE 2

| | |
|---|---|
| Icing sugar (beet) | 500 g |
| Glycerol | 500 ml |
| 2% w/v iodine in ethanol | 20 ml |

The preparation was a mustard-yellow solution of particular use as an intra-mammary infusion in the treatment of bovine mastitis.

EXAMPLE 3

| | |
|---|---|
| Icing sugar (beet) | 680 g |
| Glycerol | 520 ml |
| Iodine solution | 27 ml |

This preparation was a slightly-thickened, free-flowing, mustard-yellow smooth liquid of general use for wound-healing and similar treatment. Where the patient has, or is suspected to have, iodine sensitivity, the amount of iodine solution can be reduced by 50%.

EXAMPLE 4

| | |
|---|---|
| Icing sugar (beet) | 680 g |
| Glycerol | 520 ml |
| Iodine solution | 54 ml |

This preparation was a slightly-thickened, free-flowing, mustard-yellow smooth liquid of particular use in the treatment of dermatitis.

EXAMPLE 5

| | |
|---|---|
| Icing sugar (beet) | 680 g |
| Glycerol | 624 ml |
| Iodine solution | 27 ml |

The preparation was a mustard-yellow solution of particular use as an intra-mammary infusion in the treatment of bovine mastitis.

EXAMPLE 6

| | |
|---|---|
| Icing sugar (beet) | 500 g |
| Glycerol | 400 ml |
| Iodine solution | 20 ml |

The preparation was a mustard-yellow solution of particular use as an intra-mammary infusion in the treatment of bovine mastitis.

EXAMPLE 7

| | |
|---|---|
| Icing sugar (beet) | 500 g |
| Glycerol | 380 ml |
| Iodine solution | 20 ml |

This preparation was a slightly-thickened, free-flowing, mustard-yellow smooth liquid of general use for wound-healing and similar treatment.

EXAMPLE 8

| | |
|---|---|
| Icing sugar (beet) | 500 g |
| Glycerol | 250 ml |
| Iodine solution | 20 ml |

This preparation was a mustard-yellow smooth paste of general use for wound-healing and similar treatment.

EXAMPLE 9

| | |
|---|---|
| Icing sugar (beet) | 500 g |
| Glycerol | 350 ml |
| Weak Iodine Solution BP | 10 ml |

This preparation was a mustard-yellow smooth liquid of particular use in the treatment of mastitis.

EXAMPLE 10

| | |
|---|---|
| Icing sugar (beet) | 500 g |
| Glycerol | 250 ml |
| Weak Iodine Solution BP | 10 ml |

This preparation was a mustard-yellow smooth paste of general use for wound-healing and similar treatment.

EXAMPLE 11

| | |
|---|---|
| Icing sugar (beet) | 500 g |
| Glycerol | 250 ml |
| Weak Iodine Solution BP | 5 ml |

This preparation was a mustard-yellow smooth paste of general use for wound-healing and similar treatment.

EXAMPLE 12

The preparation of Example 7 was used to treat six human patients with deep varicose vein ulcers and one human patient with a burn. In each case, the preparation was directly applied to the wound and covered with a bandage The wound was redressed daily. In all cases, excellent and rapid wound-healing was observed. In one patient, chronic ulceration which had been resistant to standard methods of treatment for over 18 months was successfully healed.

The preparation also has been successfully used in the treatment of decubitus ulcers.

EXAMPLE 13

Preparations of Examples 1 to 11, mainly of Example 7 or, in the case of mastitis, Example 6, were used to treat several hundred animals of various species for a wide range of conditions. The species, conditions and number of animals treated are set forth in the following Tables 1 to 7. In all cases, good and rapid wound-healing resulted even in the presence of infection. In most cases, the animals treated were farm animals and, after wound dressing no special precautions were taken to care for the animal. The animals returned to the byre or field with nothing more than a dressing or, in some instances where appropriate, the wound was left open to the atmosphere. Applications were usually daily and the period of treatment ranged from 1 to 14 days depending on the circumstances but most were treated for 1 to 4 days. Virtually no side effects were seen. Only two animals (both cats) showed wet-dermatitis on the ventral abdomen but this is likely to have been the result of a pre-application surgical scrub.

TABLE 1

Species - Bovine
Types of condition and number of animals treated

| | |
|---|---|
| Teat lacerations (varying severity) | 86 |
| Black spot infection | 12 |
| Wet eczemas | 2 |
| Cornual (Horn) Amputations | 100+ |
| Digital Amputations (through phalanx II) | 6 |
| Subcutaneous and cutaneous surgical suture lines | 16 |
| Fresh lacerations - deep tissue involved | 12 |
| 7 day+ lacerations | 4 |
| Compound Fractures external fixation with well | 5 |
| Omphalo abscess (navel abscess) | 11 |
| Eye enucleations | 3 |
| Septic summer mastitis | 48 |
| Chronic lactating mastitis | 1 |
| Fracture tuber ischic ("hook-bone") | 2 |
| Popliteal abscess (deep tissue abscess) | 4 |
| Jaw fracture and bone graft | 2 |
| Hernia gauze | 4 |

TABLE 2

Species - Canine
Types of condition and number of animals treated

| | |
|---|---|
| Otitis externa (canker) | 2 |
| Wet eczema | 21 |
| Mange sarcoptic and demodectic with parenteral treatment | 4 |
| Eye enucleations 6 Mastectomy - packing dead space | 5 |
| Post spay suture lines | 24 |
| Foreleg amputations | 6 |
| Burns (abrasion and caustic) | 4 |
| Mandibular wiring (injuries from road traffic accidents) | 2 |

TABLE 3

Species - Feline
Types of conditions and number of animals treated

| | |
|---|---|
| Eye enucleations | 3 |
| Dog bites and road traffic lacerations with deep tissue involvement | 4 |
| Spays | 18 |
| Tourniquet injuries - deep tissue | 4 |
| Wet eczema | 3 |
| Abscess - digital - dorsal surface of paw | 11 |
| Mandibular abscesses | 3 |

TABLE 4

Species - ovine
Types of condition and number of animals treated

| | |
|---|---|
| Blowfly strike (dermatitis caused by greenbottle mainly in the perineal and lumbar region) | 14 |
| Caustic chemical burn (from antiseptics, etc) | 1 |
| Digital amputations | 9 |
| Lacerations - 24 hr+ - dog attack | 60 |
| Deep abscess | 6 |

TABLE 5

Species - Equine
Types of condition and number of animals treated

| | |
|---|---|
| Mid-cannon lacerations | 11 |
| Hock trauma injuries (mainly from horse boxes) | 9 |
| Fresh body skin lacerations - sutured | 7 |
| Suture lines | 14 |
| Abrasion burns - flank and gluteals | 4 |
| Idiopathic wet oedema | 1 |
| Knee ulcers (usually from trauma) | 4 |
| Harness/saddle - sores | 14 |
| Hunter's wet rash | 14 |
| Aircraft Shipping trauma injuries | 31 |

TABLE 6

Species - Avian
Types of condition and number of animals treated

| | |
|---|---|
| Drake - deep skin tissue chest wound (2 days old) | 1 |

TABLE 7

Species - Caprine
Types of condition and number of animals treated

| | |
|---|---|
| Road traffic accident fracture tib-fib flap | 1 |
| Rope burn (hobble) | 2 |
| Rope burn - deep neck | 2 |

It will be appreciated that the invention is not restricted to the particular details specified above and that numerous modifications and variations can be made without departing from the scope of the invention.

We claim:

1. A wound-healing preparation consisting of a solution or paste of powdered sucrose and elemental iodine in a vehicle consisting essentially of glycerol.

2. A preparation as claimed in claim 1, wherein the vehicle is substantially anhydrous glycerol.

3. A preparation as claimed in claim 1, wherein the sucrose concentration is 60 to 85% w/v.

4. A preparation as claimed in claim 1, wherein the iodine concentration is 0.1 to 5 wt %.

5. A preparation as claimed in claim 1, which is in the form of an infusible solution.

6. A method of treating surgical sutures which comprises coating a surgical suture with a preparation consisting of a solution or paste of powdered sucrose and elemental iodine in a vehicle consisting essentially of glycerol.

7. A method of treating a mammal suffering from mastitis comprising administering to said mammal a veterinary infusible solution consisting of powdered sucrose and elemental iodine in a vehicle consisting essentially of glycerol.

8. The method as claimed in claim 7, wherein said mastitis is bovine summer mastitis.

9. The method as claimed in claim 6, wherein the vehicle is substantially anhydrous glycerol.

10. The method as claimed in claim 7, wherein the vehicle is substantially anhydrous glycerol.

11. The method as claimed in claim 6, wherein the sucrose concentration is 60 to 85% w/v.

12. The method as claimed in claim 6, wherein the iodine concentration is 0.1 to 5 wt %.

13. The method as claimed in claim 7, wherein the sucrose concentration is 60 to 85% w/v.

14. The method as claimed in claim 7, wherein the iodine concentration is 0.1 to 5 wt %.

* * * * *